(12) United States Patent
Schiller

(10) Patent No.: US 9,963,473 B2
(45) Date of Patent: May 8, 2018

(54) STABILIZED FORM OF TETROFOSMIN AND ITS USE

(71) Applicant: ROTOP PHARMAKA GMBH, Dresden (DE)

(72) Inventor: Eik Schiller, Dresden (DE)

(73) Assignee: ROTOP Pharmaka GmbH, Dresden (DE)

( * ) Notice: Subject to any disclaimer, the term of this patent is extended or adjusted under 35 U.S.C. 154(b) by 0 days. days.

(21) Appl. No.: 15/114,658

(22) PCT Filed: Jan. 28, 2015

(86) PCT No.: PCT/EP2015/051699
§ 371 (c)(1),
(2) Date: Nov. 15, 2016

(87) PCT Pub. No.: WO2015/114002
PCT Pub. Date: Aug. 6, 2015

(65) Prior Publication Data
US 2016/0355532 A1   Dec. 8, 2016

(30) Foreign Application Priority Data

Jan. 28, 2014  (EP) .................................... 14152885

(51) Int. Cl.
| | | |
|---|---|---|
| *A61K 51/00* | (2006.01) | |
| *C07F 9/50* | (2006.01) | |
| *C07F 9/54* | (2006.01) | |
| *C07F 13/00* | (2006.01) | |
| *A61K 51/04* | (2006.01) | |

(52) U.S. Cl.
CPC ........ *C07F 9/5027* (2013.01); *A61K 51/0478* (2013.01); *C07F 9/5095* (2013.01); *C07F 9/5449* (2013.01); *C07F 13/005* (2013.01)

(58) Field of Classification Search
CPC ..................................................... A61K 51/00
See application file for complete search history.

(56) References Cited

U.S. PATENT DOCUMENTS

| | | | |
|---|---|---|---|
| 2010/0305349 A1 | 12/2010 | Barnard et al. | |
| 2015/0166587 A1* | 6/2015 | Zheng ................ | C07F 9/65688 564/82 |

FOREIGN PATENT DOCUMENTS

| | | |
|---|---|---|
| CN | 1331081 A | 1/2002 |
| DE | 102005005446 A1 | 8/2006 |
| EP | 1894938 A1 | 3/2008 |
| WO | 2010058004 A1 | 5/2010 |

OTHER PUBLICATIONS

International Search Report, issued in PCT/EP2015/051699, dated Mar. 16, 2015.

* cited by examiner

*Primary Examiner* — Michael G Hartley
*Assistant Examiner* — Jagadishwar R Samala
(74) *Attorney, Agent, or Firm* — FisherBroyles, LLP; Andrew K. Gonsalves, Esq.

(57) ABSTRACT

The present invention provides a stabilized form of Tetrofosmin, which is stable at room temperature as well as in contact with oxygen, and a non-radioactive kit containing a stabilized form of Tetrofosmin for the preparation of a radiopharmaceutical composition in the field of diagnostic radiopharmaceuticals, especially for myocardial perfusion studies in patients with coronary artery diseases and in oncology.

16 Claims, 4 Drawing Sheets

STABILIZED FORM OF TETROFOSMIN AND ITS USE

Figure 1:
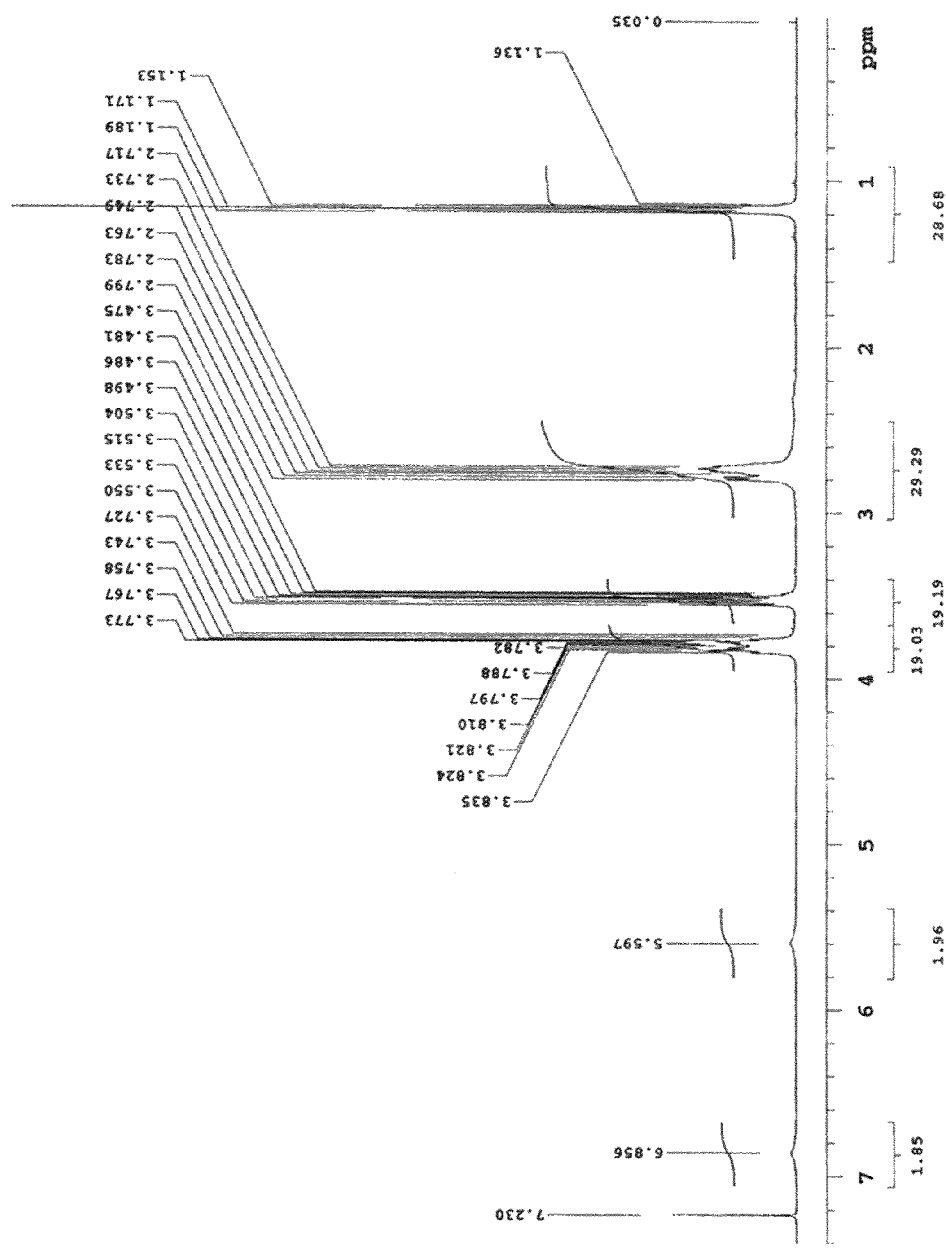

This invention relates to a stabilized form of Tetrofosmin in the field of diagnostic radiopharmaceuticals, especially for myocardial perfusion studies in patients with coronary artery diseases and in oncology.

$^{99m}$Tc-based radiopharmaceuticals are commonly used in diagnostic nuclear medicine, especially for in vivo imaging (e.g. via immunoscintigraphy or radiolabeling). Usually cold kits are manufactured in advance in accordance with strict requirements of Good Manufacturing Practice Guidelines (GMP), containing the chemical ingredients (e. g. $^{99m}$Tc-coordinating ligands, preservatives) in lyophilized form. The radioactive isotope $^{99m}$Tc ($t_{1/2}$=6 h) is added to those kits shortly before application to the patient via intravenous or subcutaneous injection.

Various $^{99m}$Tc-coordinating ligands containing coordinating phosphorus atoms with alkyl substituents and capable of forming cationic $^{99m}$Tc-complexes are known. One of the example ligand structures disclosed in EP 0 311 352 A1 is as follows:

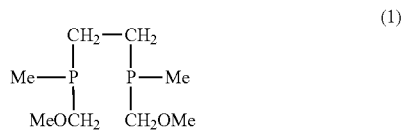

EP 0 337 654 A2 discloses $^{99m}$Tc-coordinating diphosphine ligands (L), wherein one preferred example thereof is the ether functionalized diphosphine ligand 1,2-bis[bis(2-ethoxy-ethyl)phosphino]ethane according to formula (2), called Tetrofosmin ("P53"):

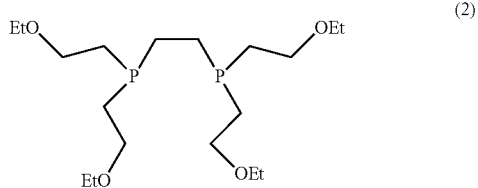 [SMILES: CCOCCP(CCOCC)CCP(CCOCC)CCOCC]

that forms a dimeric cationic technetium(V) dioxo phosphine complex, [TcO$_2$L$_2$]$^+$ with $^{99m}$Tc, useful as myocardial imaging agent.

$^{99m}$Tc-Tetrofosmin is also described to be useful for tumor diagnostics, in particular of breast cancer and parathyroid gland cancer, and for multidrug resistance (MDR) research.

With regard to EP 0 337 654 A2 a Tetrofosmin containing kit is distributed under the name Myoview™ (GE Healthcare). The kit is a one vial kit containing 0.23 mg Tetrofosmin, 0.03 mg stannous chloride dihydrate, 0.32 mg disodium sulphosalicylate, 1.0 mg sodium D-gluconate, 1.8 mg sodium hydrogen carbonate and nitrogen as protective gas. According to the manufacturer the kit has a shelf life of 35 weeks when stored at 2° C. to 8° C. and protected from light. However, due to the potential presence of too much nitrogen gas in the Myoview kit during the labeling procedure, several variances in the radiochemical purity of $^{99m}$Tc-Tetrofosmin were reported [Murray et al., *Nucl. Med. Comm.* 2000, 21, 845-849].

An optimized formulation of the Tetrofosmin kit is described in EP 1 345 630 B1. It introduces the Myoview™ 24 (GE Healthcare) preparation containing ascorbic acid (or alternatively para-aminobenzoic acid or gentisic acid) as a radioprotectant and a paraben as antimicrobial preservative.

Another optimized formulation of the Tetrofosmin kit is described in EP 1 824 525 B1. This kit primarily aims to increase post labeling stability of the of $^{99m}$Tc-Tetrofosmin complex and contains additionally ascorbic acid as stabilizer without any antimicrobial preservative. This multidose kit is a registered drug in the US under the name Myoview™ 30 (GE Healthcare) and contains 1.38 mg Tetrofosmin, 0.09 mg stannous chloride dihydrate, 1.92 mg disodium sulphosalicylate, 3 mg sodium D-gluconate, 11 mg sodium hydrogen carbonate, and 3 mg ascorbic acid. According to EP 1 824 525 B1 the Myoview™ 30 Kit has a shelf-life of 78-weeks when stored at 2° C. to 8° C. and protected from light.

WO 2009/037336 A2 relates to another $^{99m}$Tc-Tetrofosmin radiopharmaceutical composition comprising Tetrofosmin and a radioprotectant like ascorbic acid at a particular range of molar ratios.

CN 1 331 081 A discloses Tetrofosmin salts containing chloride or bromide or aryl sulfonates as negatively charged counterions, which can be used for the preparation of a $^{99m}$Tc-Tetrofosmin radiopharmaceutical composition. These salts can be stored for up to 3 months. According to CN 1 331 081 A Tetrofosmin hydrochloride is a viscous liquid. Own experiments of the inventors of the present invention revealed that the halide salts of Tetrofosmin salts are hygroscopic oils, which are complicated to handle, e.g. when weighed. The oily and hygrospcopic properties of Tetrofosmin hydrochloride hampers its use in pharmaceutical preparations. Attempts to synthesize the sulfosalicylate salt of Tetrofosmin failed because the starting material sulfosalicylic acid was not soluble in ether in the concentration specified in CN 1 331 081 A. (3.4 g in 15 ml).

WO 2007/148088 A2 discloses an ethylene-tetrafluoroethylene copolymer coating for the sealed containers in which the radiopharmaceutical compositions are provided. Aim of this invention is the reduction of the oxygen content in the headspace of the lyophilized kit formulations and the prevention of impurities leaching from the closure.

Tetrofosmin is extremely sensitive to atmospheric oxygen, which makes synthesis of the substance, as well as manufacturing and handling of the kit complicated as the substance has constantly to be handled in an oxygen free atmosphere.

High purity and stability are pivotal requirements for chemical compounds used as active ingredients in pharmaceuticals.

The objective of the invention is primarily to provide stabilized forms of Tetrofosmin, which are stable in contact with oxygen and allow an easier handling of the substance during synthesis, quality control and manufacture of the kit. Another object of the invention is to provide a kit containing a stabilized form of Tetrofosmin resulting in higher stability, e.g. a prolonged kit shelf life.

According to the present invention the objective is solved by a stabilized form of Tetrofosmin according to formula (I)

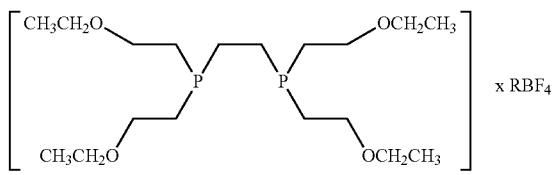

(I)

wherein x is a number between 1 and 2, more preferably 1 or 2, whereas every R is covalently attached to one phosphor atom. R is chosen from H or selected from substituted, non-substituted, linear or branched C1 to C3 alkyl residues, preferably R is H.

Preferably, the stabilized form of Tetrofosmin according to the invention is a salt selected from the following formula:

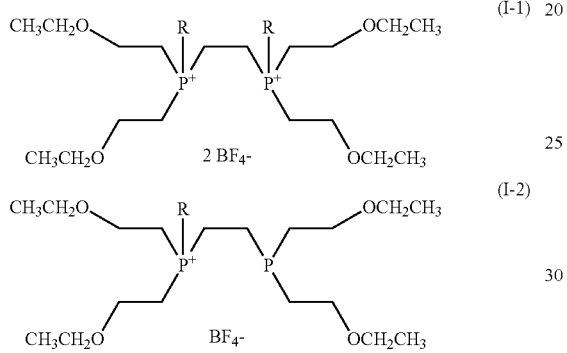

or a mixture thereof.

R is H or selected from substituted, non-substituted, linear or branched C1 to C3 alkyl residues, preferably R is H, $BF_4^-$ is the tetrafluoroboronanion.

Preferably the stabilized form of Tetrofosmin according to formula (I) is the bis-phosphonium tetrafluoroborate salt of Tetrofosmin.

Advantageously a stabilized form of Tetrofosmin according to the invention is solid, stable at room temperature without any need of storage under inert conditions. Moreover, the salt of the stabilized form of Tetrofosmin according to the invention rapidly dissolves when coming in contact with an aqueous solution (e.g. saline solution, pertechnetate solution). Preferably a stabilized Tetrofosmin salt according to the invention can be readily transformed back to the free Tetrofosmin ligand at a pH>7, more preferably between 7.5 and 9.0.

Furthermore, the stabilized form of Tetrofosmin according to the invention is not hygroscopic in nature so it does not tend to cake or become liquid when exposed to air humidity. At the same time, the stabilized form of Tetrofosmin as a stabilized solid can be precisely weighed under normal GMP conditions, e.g. laminar air-flow, without degradation. In this way, the solid aggregate state of the stabilized form of Tetrofosmin advantageously provides rapid and easy handling in comparison to hitherto available forms of Tetrofosmin.

Additionally, the stabilized form of Tetrofosmin according to the invention directly reacts with pertechnetate ($^{99m}TcO_4^-$) to form a technetium-Tetrofosmin complex in high radiochemical yield of ≥90% (in compliance with the United States Pharmacopeial monograph of $^{99m}Tc$-Tetrofosmin).

It has also surprisingly been found that the negatively charged counterion $BF_4^-$ of the stabilized form of Tetrofosmin according to the invention does not form any complex structures with a radioactive metal ion, preferably technetium ions, so that the complex content is below the limit of detection by methods of analysis.

Preferably in a salt according to the invention the molar ratio of tetrafluoroborate anion to the Tetrofosmin phosphonium cation is in a range from 2:1 to 1:1.

Preferably the stabilized form of Tetrofosmin according to the invention has the following formula (II):

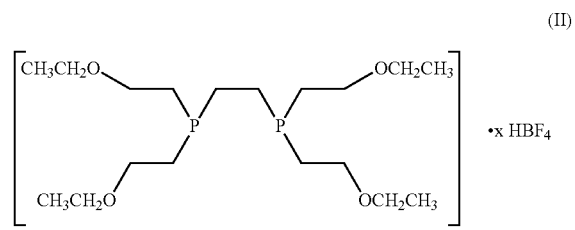

(II)

wherein x is a number between 1 and 2, more preferably 1 or 2.

More preferably, the stabilized form of Tetrofosmin according to the invention is a salt selected from the following formula:

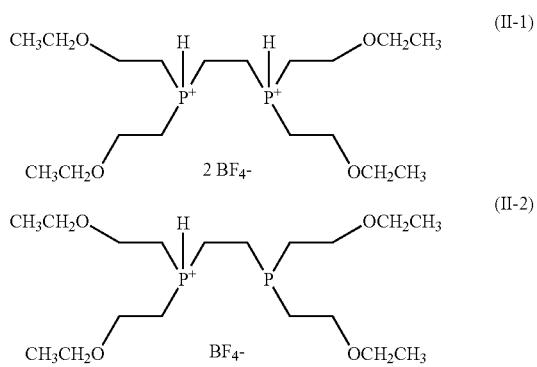

or a mixture thereof.

The stabilized form of Tetrofosmin according to the invention is obtained by chemical conversion of Tetrofosmin with fluoroboric acid.

Thus, the present invention also includes a process to obtain a stabilized form of Tetrofosmin according to the invention with the steps:
 a) adding fluoroboric acid (also named tetrafluoroboric acid, $HBF_4$) to Tetrofosmin,
 b) isolating a stabilized form of Tetrofosmin according to the invention from the reaction mixture.

Preferably, the stabilized form of Tetrofosmin according to the invention is obtained by adding fluoroboric acid (also named tetrafluoroboric acid; $HBF_4$) after completing the Tetrofosmin synthesis or to commercially available Tetrofosmin.

Tetrofosmin can be synthesized under overpressure conditions and under oxygen-free atmosphere according to EP 1 824 525 B1 (cf. example 1) or EP 0 337 654 A2. The usual synthesis involves reacting ethyl vinyl ether with 1,2-bis (poshino)ethane using α-azoisobutyronitrile as a free radical initiator. Tetrofosmin can also be obtained by chemical synthesis, such as those disclosed by Reid et al. (*Synth. Appl. Isotop. Lab. Comp.* 2006, 7, 252-255).

When adding the fluoroboric acid (HBF$_4$), the Tetrofosmin or a solution containing Tetrofosmin should preferably be substantially free of enol ethers (like ethyl vinyl ethers) to avoid side reactions. Thus, when Tetrofosmin is used directly after synthesis from ethyl vinyl ether with 1,2-bis (phosphino)ethane, an excess of ethyl vinyl ether should be removed, e. g. by evaporation.

By the term "substantially free of enol ethers" it is understood that the content of enol ether in the Tetrofosmin or a solution containing Tetrofosmin when adding the tetrafluoroborate or fluoroboric acid is below the limit of detection by methods of analysis, preferably below 1 percent, more preferably 0.1 percent by weight of Tetrofosmin and therefore trace amounts of enol ether contaminants cannot be excluded.

Alternatively, a stabilized form of Tetrofosmin according to the invention can be obtained, when adding a strong acid (e. g. HCl) to Tetrofosmin or a solution containing Tetrofosmin. Subsequently a tetrafluoroborate salt (e. g. sodium tetrafluoroborate) can be added, and vice versa.

Preferably, HBF$_4$ is added in the form of an aqueous solution of HBF$_4$ or alternatively an organic solution of HBF$_4$. Preferably, the organic solution comprises ether as solvent, more preferably alkyl ether, such as diethyl ether.

If a solution of HBF$_4$ is added to pure Tetrofosmin, the bis-phosphonium tetrafluoroborate salt according to the invention can be extracted from this solution in high yield, preferably >80%, and in high purity.

In the process according to the invention a solution of HBF$_4$ is used as boron (B) and fluorine (F) containing reactant. The concentration of the HBF$_4$ solution used herein does not appear to be critical. Preferably, the solution of HBF$_4$ employed comprises at least 30 percent, more preferably at least 40 percent and up to 50 percent by weight of HBF$_4$.

Particularly surprising is the finding that the stabilized form of Tertrofosmin according to the invention is soluble in organic solvents (e. g. methylene chloride, chloroform or methylethyl ketone), which permits selective enrichment of the stabilized form of Tetrofosmin as a salt in the organic phase.

For example, Tetrofosmin (e. g. obtained by chemical synthesis) is practically first dissolved in an organic solvent, preferably an aprotic organic solvent (e. g. methylene chloride, chloroform or methylethyl ketone) and an aqueous solution of HBF$_4$ is added to the solution under vigorously stirring. After a short reaction time, preferably less than 10 minutes, the reaction yields substantially quantitative conversion, so that the organic phase containing the stabilized form of Tetrofosmin according to the invention can be separated from the reaction mixture and the organic solvent is removed by evaporation. Subsequently, the product is dried in vacuum.

Advantageously the stabilized form of Tetrofosmin has a purity over 96%, in particular over 99%, which makes it directly suitable for pharmaceutical use. There is no need for purification.

The stabilized form of Tetrofosmin according to the invention, which is preferably in the protonated form, is advantageously stable when stored at air and room temperature, at least for several months, preferably at least for one year.

The stabilization of Tetrofosmin according to the invention by the addition of HBF$_4$ has thus the advantage that the manufacture of a kit with either of the stabilized salts can be carried out under normal GMP conditions, e.g. laminar air-flow. Furthermore, the stabilized Tetrofosmin as active pharmaceutical ingredient can be stored for prolonged time and handled without degradation, advantageously at room temperature and in the presence of air-oxygen.

As used herein, the term "room temperature" refers to a temperature of 15° C. to 30° C., more preferably 20±5° C.

Where reference is made hereinabove and herein below to documents, these are incorporated insofar as is necessary.

The general terms used herein above and herein below preferably have the meanings given herein below.

Object of the invention is also a non-radioactive kit for the preparation of a radiopharmaceutical composition, comprising at least one container, wherein one container contains:
  (i) a stabilized form of Tetrofosmin according to the invention.

Preferably the kit comprises one or several additional ingredients selected from:
  (ii) reductant, preferably a tin(II) salt,
  (iii) transfer ligand, such as gluconate and/or sulphosalicylate,
  (iv) preservative,
  (v) agents for pH adjustment, such as hydrogen carbonate or phosphate salts and
  (vi) fillers.

Whilst components (i) to (iii) are preferably comprised in the kit, components (iv) to (vi) are optionally.

The kit preferably comprises the stabilized form of Tetrofosmin according to the invention in powder form, more preferably in a freeze-dried powder form.

In contrast to previously known kits containing Tetrofosmin in lyophilized form, such as described in EP 0 337 654 A2 or EP 1 824 525 B1, a non-radioactive kit according to the invention can be stored at room temperature for at least 52 weeks without degradation, advantageously resulting in a more economic kit manufacturing process (e.g. larger batch size) minimization of transport and storage costs.

Preferably, the stabilized form of Tetrofosmin in the non-radioactive kit is the protonated form, as depicted in formula (II):

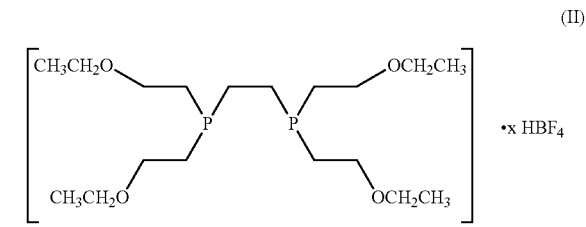

(II)

with x as defined above.

In the present invention the kit preferably comprises of one sterile container. The sterile containers enable maintain sterility of the pharmaceutical formulations, facilitate transportation and storage, and allow administration (e. g. intravenous) of the pharmaceutical formulations without prior sterilization step.

Preferably, the container is a sealed and sterilized container selected from a group comprises vial, syringe bottle, or ampoule, wherein the container may come in of various sizes and capacities. For example, the container may comprise between 1 and 50 mL, preferably between 5 and 25 mL, more preferably between 10 and 20 mL of the pharmaceutical composition.

Preferably, the formulation of a non-radioactive kit is produced by mixing all ingredients in an aqueous solution. The formulation may then be sterile filtered, e.g. through a sterile 0.2 μm filter. The formulation is preferably filled into sterile containers. The containers are subsequently sealed and optionally lyophilized. This is preferably performed by first partially sealing the containers, followed by lyophilization and subsequently sealing and capping.

When the pertechnetate solution is added to the non-radioactive kit according to the invention, the desired $^{99m}$Tc Tetrofosmin complex is formed in high yield (≥90%) within 15 minutes at room temperature. When stored at room temperature it has a usable shelf-life of at least 6 hours, more preferably of 12 hours or more.

A "reductant" is a reducing agent, which is suitable for reducing technetium being in a high oxidation state (e. g. pertechnetate Tc(VII)), to lower oxidation states of technetium, which is used for in vivo studies. To ensure that all of the pertechnetate is converted to a lower oxidation state, preferably, in a kit according to the invention, a reductant is in a molar excess to a $^{99m}$Tc-compound. Suitable reductants are selected from the group of sodium dithionite, sodium bisulphite, ascorbic acid, formamidine sulphinic acid, tin, iron(II) or copper(I). Preferably, a powerful reductant preferably comprises stannous ions, metallic tin or an alloy thereof. Preferably, a kit comprises tin ions in form of tin(II), wherein the salts of tin(II) is preferably selected from stannous chloride dihydrate or stannous tartrate.

Preferably, the mass fraction of the reductant used in the non-radioactive kits of the present invention is suitably between 1 to 15% (w/w), more preferably between 4 to 10% (w/w) based on the total weight of the stabilized form of Tetrofosmin.

Mass fraction is herein defined as the weight of a solid component (w) per weight of the total weight of the stabilized form of Tetrofosmin (w) in a single unit or multiple unit patient dose kit. The mass fraction is independent of the content of a filler or agent for pH adjustment.

A "transfer ligand" is an ancillary chelating compound which reacts rapidly with technetium or pertechnetate to form a weak complex, wherein the transfer ligand can be displaced by Tetrofosmin. They are also referred to as transchelators or intermediate ligands. The presence of a transfer ligand minimizes the risk of formation of reduced hydrolysed technetium (RHT) due to rapid reduction of pertechnetate competing with technetium complexation. Suitable such transfer ligands are salts of organic acids with a biocompatible cation, preferably "weak organic acids" having a pKa in the range 3 to 7. Suitable weak organic acids are selected from acetic acid, citric acid, tartaric acid, gluconic acid, glucoheptonic acid, benzoic acid, phenols or phosphonic acids. Hence, suitable salts are acetates, citrates, tartrates, gluconates, glucoheptonates, benzoates, phenolates or phosphonates. Preferred such salts are tartrates, gluconates, glucoheptonates, benzoates. Most preferably, a transfer ligand is a salt of gluconic acid, with a biocompatible cation, especially sodium gluconate. Additional preferred transfer ligands are selected from dimercaptosuccinic acid, hexamethylpropyleneamine oxime, mercaptoacetyltriglycine, 5-sulfosalicylic acid or salts thereof with biocompatible cations. Two or more transfer ligands may be used in combination, and the Tetrofosmin kits of the present invention most preferably comprise a combination of 2-hydroxy-5-sulfo-benzoic acid, disodium salt, trihydrate (disodium 5-sulfosalicylate) and sodium gluconate.

Preferably, the mass fraction of the transfer ligands used in the non-radioactive kits of the present invention is suitably between 10 to 600% (w/w), more preferably between 50 to 500% (w/w), most preferably between 50 to 300% (w/w) based on the total weight of the stabilized form of Tetrofosmin.

As explained above the labeling reaction to form a technetium complex can be performed under acidic conditions, preferably above pH 4. Thus there is no need for an agent for pH adjustment in the kit. In this case the technetium-Tetrofosmin complex is formed with pertechnetate ($[^{99m}Tc]TcO_4^-$) under acidic pH conditions (pH of 7.0 or less), preferably in a pH range between pH 2.0 and 6.0, more preferably between 3.0 and 5.0. This acid solution is generally acceptable for human or mammalian administration.

Nevertheless, the non-radioactive kit according to the invention preferably comprises an agent for pH adjustment to adjust the pH of a radiopharmaceutical composition within preferred ranges (approximately pH 4.0 to 10.0), more preferably nearer to or within the physiological pH range, which is preferred for human or mammalian administration and lies between pH 6 and 9.5, preferably between 7.5 and 9.0. Preferably, agents for pH adjustment or pH regulating agents comprise sterile solutions or sterile powders of the salts.

The agent for pH adjustment preferably comprises a member selected from the group consisting of pharmaceutically acceptable buffers or agents for pH adjustment, such as citrate, hydrogen and/or sodium carbonates, hydrogen phosphates, TRIS, tricine or mixtures thereof. A preferred agent for pH adjustment for the kits according to the invention is a salt of carbonic acid, like carbonate or hydrogen carbonate, more preferably sodium hydrogen carbonate ($NaHCO_3$).

In case the non-radioactive kit according to the invention comprises a buffer or agent for pH adjustment, the buffer or agent for pH adjustment is preferably not in the same container as the stabilized form of Tetrofosmin according to the invention. Hence for technetium labeling first the stabilized form of Tetrofosmin according to the invention mixed with additional ingredients is dissolved by adding a solution of the buffer or an agent for pH adjustment. Subsequently, the pertechnetate solution to form the technetium-Tetrofosmin complex is added.

Likewise, the optional buffer or agent for pH adjustment can be added to the radiopharmaceutical composition after the radiolabeling procedure is finished.

The term "filler" as used herein refers to a pharmaceutically acceptable bulking agent, which may facilitate material handling during production of a kit or a radiopharmaceutical composition thereof. Suitable fillers include inorganic salts such as sodium chloride, and water soluble sugars or sugar alcohols such as sucrose, maltose, D(−)-mannitol or trehalose. Certain buffer salts or agents for pH adjustment may also function as bulking agents.

The mass fraction of the filler used in the non-radioactive kits of the present invention is chosen freely, but is typically in the range between 1 to 30 mg, more preferably between 5 to 25 mg based on the total weight of the stabilized form of Tetrofosmin.

In addition, if desired or necessary, the non-radioactive kit of the present invention optionally further contains pharmaceutically acceptable preservatives to prevent decomposition of organic matter, e. g. due to microbial contamination, so that the formulation of a kit products that can be stored for long periods of time.

The preservatives are preferably selected from the group consisting ascorbic acid, benzyl alcohol, cresol; cetrimide, thiomersal, phenol and the parabens (e. g. methyl, ethyl, propyl or butyl paraben or mixtures thereof).

Preferably, a kit according to the invention comprises at least one container.

In a particular preferred non-radioactive kit the container contains:
(i) a stabilized form of Tetrofosmin according to formula (I), preferably the tetrafluoroborate salt of Tetrofosmin according to formula (II),
(ii) a reductant, preferably a tin(II) salt,
(iii) one or more transfer ligands, preferably gluconate and sulphosalicylate
(iv) optionally a filler, preferably D(-)-mannitol.

In this case a non-radioactive kit preferably comprises only one container,
wherein all components, contained therein, are available in solid form, and
wherein the technetium complex is preferably formed by dissolving the content of the container with a pertechnetate solution.

In a particularly preferred embodiment of the invention, the non-radioactive kit comprises:
1) a first container containing:
(i) a stabilized form of Tetrofosmin according to the invention, preferably the tetrafluoroborate salt of Tetrofosmin according to formula (II),
(ii) a reductant, preferably a tin (II) salt,
(iii) one or more transfer ligands, preferably gluconate and sulphosalicylate
(iv) optionally a filler, preferably D(-)-mannitol.
2) a second container comprising:
(i) a buffer or agent for pH adjustment, preferably a salt of carbonic acid, like carbonate or hydrogen carbonate, (as powder or solution).

In this case the technetium complex is preferably formed by first adding to the first container the content of the second container, thus releasing the free Tetrofosmin ligand. In case of a powdery buffer or agent for pH adjustment, a diluent comprising water, preferably water for injections or a saline solution (sterile solution of sodium chloride) is added to the second vial prior to adding the content to the first vial. Subsequently the pertechnetate solution is added to the mixture of the first and the second vial, resulting in the formation of a pharmaceutical formulation for intravenous administration.

Alternatively the technetium complex is formed by adding the pertechnetate solution to the first container and immediately or after labeling is finished transferring the content of the second container to the first container.

In another preferred embodiment of the invention, the non-radioactive kit comprises:
1) a first container containing:
(i) a stabilized form of Tetrofosmin according to the invention, preferably the tetrafluoroborate salt of Tetrofosmin according to formula (II),
(ii) optionally a filler, preferably D(-)-mannitol.
2) a second container comprising:
(i) a reductant, preferably a tin (II) salt,
(ii) one or more transfer ligands, preferably gluconate and sulphosalicylate
(iii) an agent for pH adjustment, preferably hydrogen carbonate Again the technetium complex is preferably formed by first mixing the content of the first container and the second container after the addition of a biocompatible diluent comprising water, preferably water for injections or a saline solution (sterile solution of sodium chloride), followed by adding the pertechnetate solution resulting in the formation of a pharmaceutical formulation for intravenous administration.

Alternatively the technetium complex is formed by adding the pertechnetate solution to the second container and subsequently transferring the content of the second container to the first container. Likewise the technetium complex is formed by adding the pertechnetate solution to the first container and subsequently transferring the content of the first container to the second container.

The non-radioactive kit according to the invention can be formulated as single dose kit or multi dose kit. Preferably the kit is a multi dose kit, which comprises sufficient material for multiple patient doses from the same radiopharmaceutical composition.

As described above the multi dose kit comprises at least one container, preferably one or two different containers. Preferably at least one container contains the stabilized form of Tetrofosmin according to the invention in a sufficient amount so that preferably 2 to 20 single unit patient doses of a radiopharmaceutical composition, comprising the $^{99m}$Tc-tetrofosmin complex, can be obtained.

Advantageously, due to the usable shelf-life of the $^{99m}$Tc-Tetrofosmin complex of at least 6 hours, more preferably of at least 12 hours, when adding the pertechnetate solution to the multiple unit patient dose kit, a radiopharmaceutical composition can be prepared on a centralized basis, distributed to the clinics and subsequently applied to the patients, which reflects a typical clinical situation.

The invention comprises also the use of a stabilized form of Tetrofosmin according to the invention or a kit according to the invention for manufacturing a complex of Tetrofosmin with a radioactive metal, preferably technetium.

Preferably the Tetrofosmin-technetium complex has the following formula:

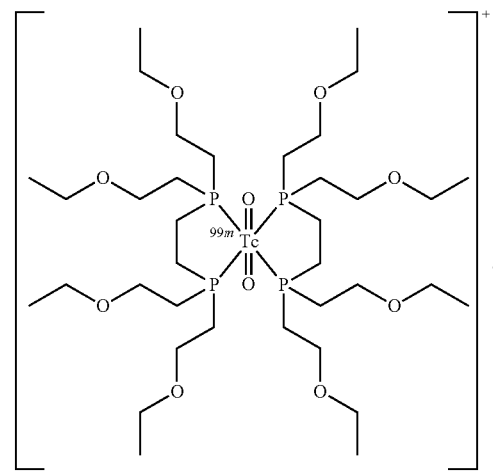

In another aspect, it is a matter according to the invention to provide a radiopharmaceutical composition comprising:
1. a stabilized form of Tetrofosmin according to the invention,
2. a Tetrofosmin-technetium complex in a biocompatible diluent comprising water, preferably a saline solution, wherein the $^{99m}$Tc labeled complex of Tetrofosmin in the radiopharmaceutical composition comprises a radioactive concentration in the range between 0.05 and 10.0 GBq/ml, more preferably between 0.1 and 3.0 GBq/ml.

The radioactive concentration is defined as the technetium-99m radioactivity (GBq) per volume of the (biocompatible) diluent (ml), comprising the Tetrofosmin-technetium complex.

The term "radiopharmaceutical composition" has its conventional meaning, and describes herein a radioactive pharmaceutical, which is formed when mixing the content of a non-radioactive kit according to the invention with a pertechnetate solution. Radiopharmaceutical compositions are suitable for intravenous administration to the mammalian, especially human body and can preferably be used for diagnostic imaging or radiotherapy, more preferably for diagnostic imaging.

Preferably kits according to the invention are used for the preparation of $^{99m}$Tc radiopharmaceuticals, wherein the radioactive metal complex (preferably $^{99m}$Tc-Tetrofosmin) is formed, preferably in the clinic, by adding a pertechnetate solution into one of the containers. Advantageously, these kits permit the user to maintain stocks of sterile and non-radioactive containers, containing the necessary ligands as a thermo-stable salt.

Surprisingly, it has been found that in a kit containing a stabilized form of Tetrofosmin according to the invention the radioactive metal complex (preferably $^{99m}$Tc-Tetrofosmin) is rapidly formed in high radiochemical yield when brought in contact with a solution containing a radioactive metal, preferably a pertechnetate solution.

Preferably the pertechnetate solution is an isotonic aqueous solution of pertechnetate $[^{99m}TcO_4]^-$, e. g. the eluent from a technetium generator.

The radioactive content of $^{99m}$Tc-pertechnetate in a pertechnetate solution to be used for the addition to the components containing in a non-radioactive kit according to the invention is suitable up to 20 GBq, preferably to 5 to 15 GBq.

The radioactive metal complex is preferably formed at room temperature, when preferably employing a gluconate transfer ligand, wherein the formation of the desired $^{99m}$Tc Tetrofosmin complex is normally completed within a complexation time of 15 minutes.

The invention also comprises the medical use of the stabilized form of Tetrofosmin or kit according to the invention, in particular in a method of diagnostics of the heart by administration of (a suitable dose of) the radioactive metal complex of Tetrofosmin (preferably $^{99m}$Tc-Tetrofosmin) to a patient. Intravenous administration of the radioactive metal complex preferably leads to a rapid myocardial uptake of the radioactive metal complex, and rapid blood, liver and lung clearances, so that the radioactive metal complex can be used for radiopharmaceutical diagnostic imaging, preferably suitable for in vivo heart imaging. When rest and stress injections are administered on the same day, a kit according to the invention preferably comprises sufficient material for multiple patient doses.

The invention is illustrated by the following examples and figures without representing a restriction of the scope of protection defined in the claims.

Caution: Due to the radiation of the nuclear isotope $^{99m}$Tc, appropriate protective measures must be taken, when handling $^{99m}$Tc compounds.

FIG. 1: $^1$H-NMR spectrum of Tetrofosmin x 2 HBF$_4$.

Figure 2:
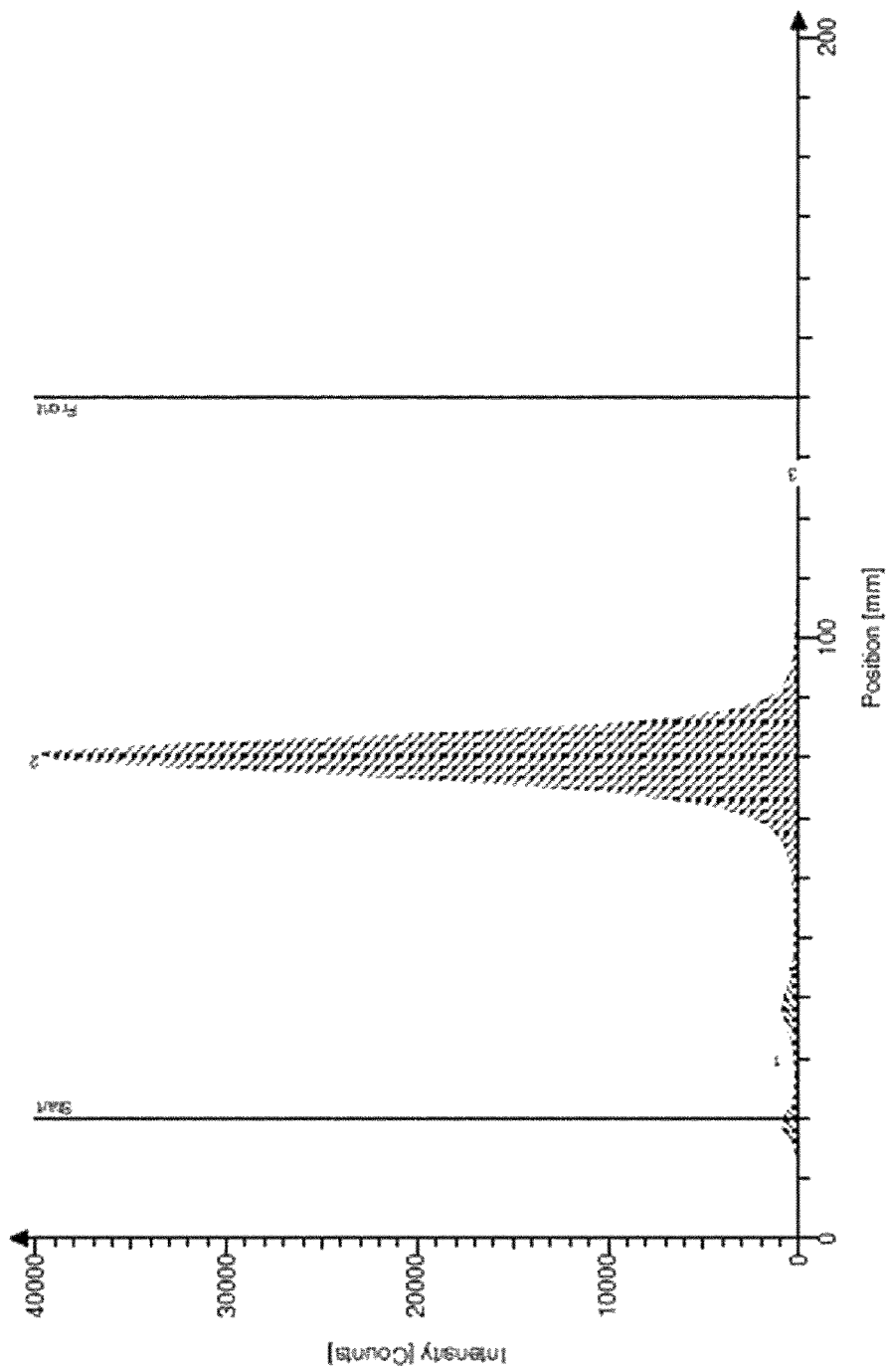

FIG. 2: TLC (thin layer chromatography) chromatogram of Tc-99m labeled Tetrofosmin using a non-radioactive kit that comprises one container and D-(−)-mannitol as filler.

Figure 3:
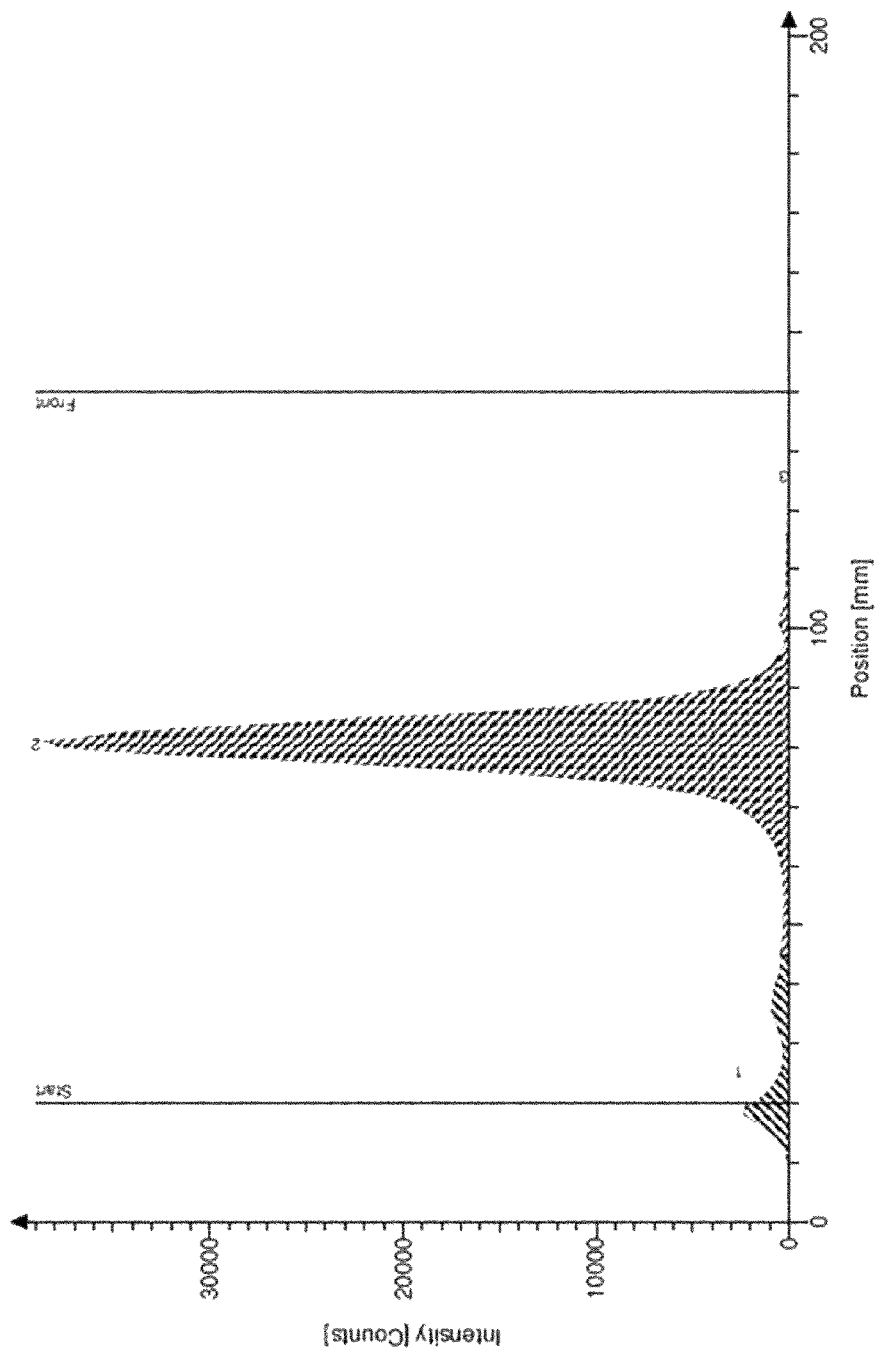

FIG. 3: TLC (thin layer chromatography) chromatogram of Tc-99m labeled Tetrofosmin using a non-radioactive kit that comprises two containers.

Figure 4:
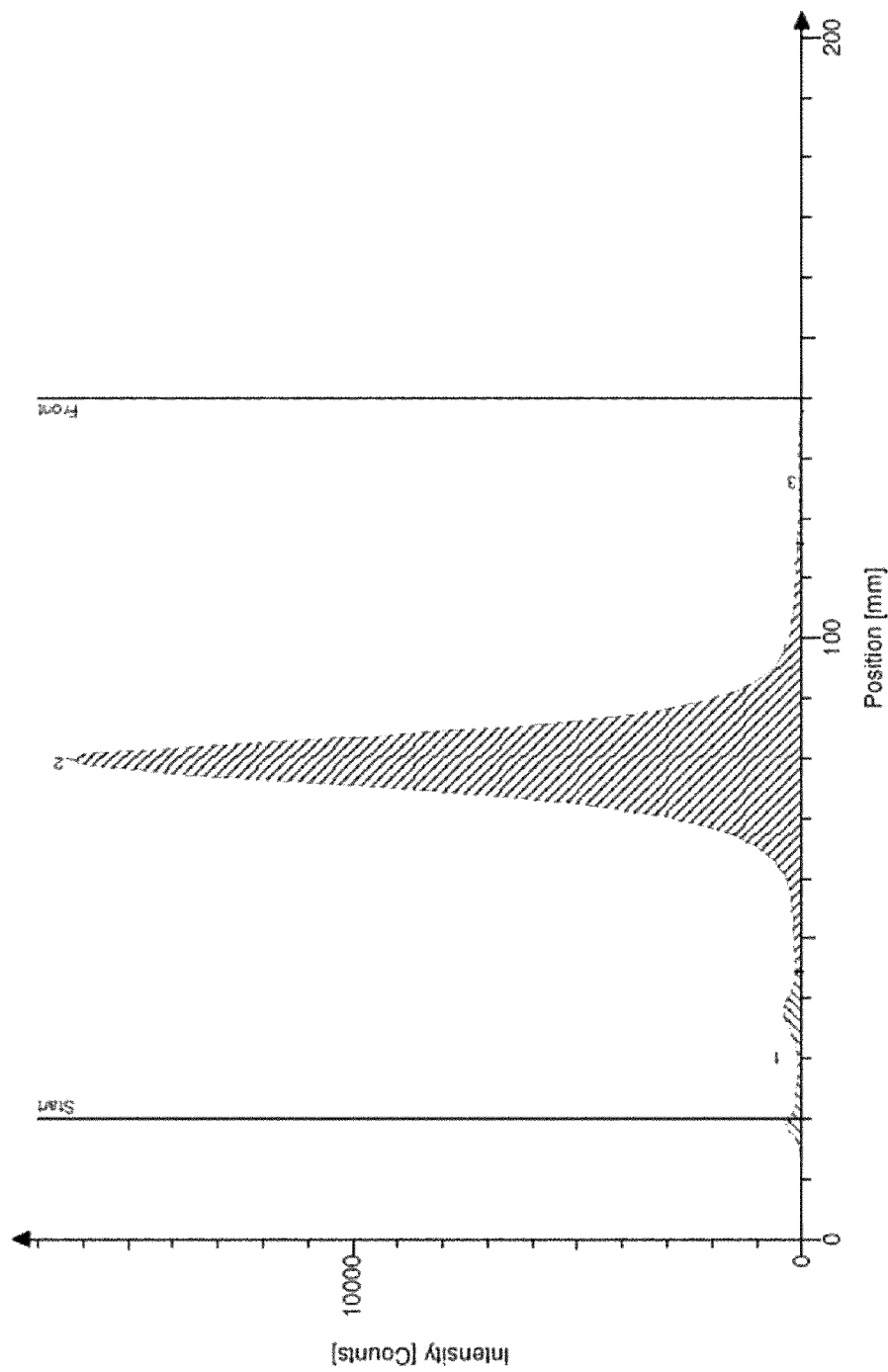

FIG. 4: TLC (thin layer chromatography) chromatogram of Tc-99m labeled Tetrofosmin using a non-radioactive kit that comprises two containers and D-(−)-mannitol as filler.

EXAMPLE 1 SYNTHESIS OF THE TETRAFLUOROBORATE SALT OF TETROFOSMIN (TETROFOSMIN X 2 HBF$_4$)

Under N$_2$ atmosphere an autoclave container is charged with 1 g (10.5 mmol) 1,2-bisphosphinoethane, 7 mL ethylvinylether (72.3 mmol) and 19.6 mg (0.12 mmol) azobisisobutyronitrile (AIBN). The reaction mixture is stirred in an oil bath at a temperature of 75° C. to 80° C. for 3 hours. The reaction mixture is then transferred in a two-neck flask. The ether is removed in a N$_2$ stream. Subsequently 30 mL methylene chloride and 3.0 mL 8 N (mol/L) aqueous HBF$_4$ solution are added under vigorous stirring. The organic phase is separated and the solvent is removed with a rotary evaporator. The remaining clear colorless oil is further dried in vacuum over night. Yield: 5.268 g (89.9%) white solid.

As shown below, the stabilized Tetrofosmin x 2 HBF$_4$ was analysed by $^1$H, $^{31}$P and $^{19}$F NMR as well as by elemental analysis. The $^1$H-NMR spectrum of Tetrofosmin x 2 HBF$_4$ is depicted in FIG. 1.

$^{31}$P NMR (ppm, CDCl$_3$): 16.92 (s); 16.93 (s)

$^1$H NMR (ppm, CDCl$_3$): 1.17 (t, J=7.2 Hz, 12H, CH$_3$), 2.76 (m, 12H, PCH$_2$), 3.53 (m, 8H, OCH$_2$), 3.77 (m, 8H, OCH$_2$), 6.23 (d, J=503.6 Hz, 2H, PH)

$^{19}$F NMR (ppm, CDCl$_3$): 150.2 (m)

Elemental analysis: found (calc.): C, 39.0% (38.7%) H, 7.69% (7.59%)

Tetrofosmin x 2 HBF$_4$ was characterized to have purity over 99% ($^1$H qNMR with dimethyl-malonic acid as internal standard), which makes it directly suitable for pharmaceutical use without the need of further purification.

EXAMPLE 2 STABILITY OF TETRAFLUOROBORATE SALT OF TETROFOSMIN

Tetrofosmin x 2 HBF$_4$ was stored at room temperature without protective gas (e. g. argon or nitrogen). In accordance to example 1, the $^1$H and $^{31}$P spectra were unchanged after 12 months.

Moreover, Tetrofosmin x 2 HBF$_4$ was heated in a normal atmosphere (with oxygen) at 50° C. for 6 hours. The $^1$H and $^{31}$P spectra showed no sign of degradation.

An open vial of Tetrofosmin x 2 HBF$_4$ was stored at room temperature, normal atmosphere and 50% humidity. After 72 h no change of weight was observed indicating the non-hygroscopic nature of the compound

EXAMPLE 3 ONE-VIAL KIT FORMULATION WITH TETRAFLUOROBORATE SALT OF TETROFOSMIN

Tetrofosmin x 2 HBF$_4$ is labeled by using a kit comprising the following composition:

| | |
|---|---|
| 0.34 mg | Tetrofosmin x 2 HBF$_4$ |
| 0.32 mg | disodium sulfosalicylate |
| 1.0 mg | sodium D-gluconate |
| 20 mg | D-(−)-mannitol |
| 0.03 mg | SnCl$_2$ x 2 H$_2$O |

The kit is labeled in approx. 3.5 mL pertechnetate eluate with 300 MBq $^{99m}$Tc at pH 4-5 and room temperature. The mixture was gently swirled until complete dissolution of the powder. The solution was left for 15 min. Radio-TLC (tin layer chromatography) was performed silica acid (ITLC-SA) using a solvent mixture of acetone and dichloromethane (65:35 v/v). Each component (peak) is characterized by a relative front ($R_f$) values, which is defined as the ratio of component position [mm] to the total distance traveled by the solvent front.

TLC revealed a radiochemical yield of 95.7% of a $^{99m}$Tc-Tetrofosmin complex and a purity of 96.1% after 6 hours at room temperature. Only traces of pertechnetate are detected. The corresponding TLC (thin layer chromatography) chromatogram of the $^{99m}$Tc labeled Tetrofosmin is shown in FIG. 2.

EXAMPLE 4 TWO-VIAL KIT FORMULATION WITH TETRAFLUOROBORATE SALT OF TETROFOSMIN

Tetrofosmin x 2 $HBF_4$ is labeled by using a kit comprising to vials, which have the following composition:

| Vial I | 0.34 mg | Tetrofosmin x 2 $HBF_4$ |
|---|---|---|
| | 0.32 mg | disodium sulfosalicylate |
| | 1.0 mg | Sodium D-gluconate |
| | 0.03 mg | $SnCl_2$ x 2 $H_2O$ |
| Vial II | 3.6 mg/mL | Sodium hydrogen carbonate (saline) |

The kit was labeled by adding a 0.5 mL aliquot of vial II (1.8 mg $NaHCO_3$) to vial I with a syringe. The kit was gently swirled until complete dissolution of the powder. Subsequently, 3.5 mL technetium-99m pertechnetate eluate (450 MBq) was added resulting in a pH of 7-8. After swirling again, the solution was left for 15 min. According to example 3, the radio-TLC was performed with ITLC-SN acetone: dichloromethane (65:35).

TLC revealed a radiochemical yield of 93.2% of a $^{99m}$Tc-Tetrofosmin complex and a purity of 94.6% after 6 hours at room temperature. The corresponding TLC (thin layer chromatography) chromatogram of the $^{99}$mTc labeled Tetrofosmin is shown in FIG. 3.

EXAMPLE 5 TWO-VIAL KIT FORMULATION WITH TETRAFLUOROBORATE SALT OF TETROFOSMIN AND FILLER

In one especially preferred kit formulation the kit comprising to vials, which comprises the following composition:

| Vial I | 0.34 mg | Tetrofosmin x 2 $HBF_4$ |
|---|---|---|
| | 0.32 mg | disodium sulfosalicylate |
| | 1.0 mg | Sodium D-gluconate |
| | 0.03 mg | $SnCl_2$ x 2 $H_2O$ |
| | 10.0 mg | D-(-)-Mannitol |
| Vial II | 9.0 mg/mL | Sodium hydrogen carbonate (saline) |

The kit was labeled by adding a 0.5 mL aliquot of vial II (4.5 mg $NaHCO_3$) to vial I with a syringe. The kit was gently swirled until complete dissolution of the powder. Subsequently, 3.5 mL technetium-99m pertechnetate eluate (3 or 10.5 GBq, respectively) was added, resulting in a pH of approximately 8. After swirling again, the solution was left for 15 min. According to example 3, the radio-TLC was performed with ITLC-SN acetone: dichloromethane (65:35).

TLC revealed radiochemical yields of the respective sample forming the $^{99m}$Tc-Tetrofosmin complex (x=2) after 15 min, 30 min and 6 hours at room temperature.

| | Radioactivity Concentration | |
|---|---|---|
| | 3 GBq/4 mL | 10.5 GBq/4 mL |
| t0 (15 min): | 92.7% | 93.2% |
| t = 30 min | 96.2% | 96.2% |
| t = 6 h | 97.9% | 97.8% |

An exemplary TLC (thin layer chromatography) chromatogram of the $^{99m}$Tc labeled Tetrofosmin is shown in FIG. 4.

EXAMPLE 6 COMPARISON OF TC-99M LABELED KIT FORMULATION CONTAINING TETRAFLUOROBORATE SALT OF TETROFOSMIN WITH A KIT FORMULATION CONTAINING NON-STABILIZED TETROFOSMIN

Biodistribution was determined after technetium-99m labeling of different formulations containing stabilized or non-stabilized Tetrofosmin. Aliquots of each solution were intravenously injected into a tail vein of male Wistar rats. Biodistribution was determined 2 min, 60 min and 24 h p.i. (four animals at each time point). The following tables reveal that biodistribution pattern is essentially the same for all three tested formulations. Hence, the identical technetium-99m Tetrofosmin complex was formed equally either from stabilized or non-stabilized Tetrofosmin.

Technetium-99m labeled kit formulation with non-stabilized Tetrofosmin—Myoview™

The commercial available product Myoview™ (GE Healthcare) was used as a comparative example:

| | 2 min | | 60 min | | 24 h | |
|---|---|---|---|---|---|---|
| organ | % ID/ organ | stdev | % ID/ organ | stdev | % ID/ organ | stdev |
| blood | 0.14 | 0.131 | 0.017 | 0.006 | 0.001 | 0.001 |
| brain | 0.04 | 0.034 | 0.021 | 0.006 | 0.003 | 0.001 |
| pancreas | 0.30 | 0.273 | 0.301 | 0.118 | 0.018 | 0.010 |
| spleen | 0.31 | 0.269 | 0.157 | 0.052 | 0.007 | 0.001 |
| kidney | 7.58 | 1.011 | 2.972 | 2.053 | 0.074 | 0.007 |
| fat | 0.03 | 0.029 | 0.040 | 0.017 | 0.001 | 0.001 |
| muscle | 0.22 | 0.199 | 0.227 | 0.125 | 0.170 | 0.038 |
| heart | 1.64 | 0.101 | 1.044 | 0.514 | 0.139 | 0.022 |
| lung | 0.79 | 0.080 | 0.241 | 0.516 | 0.024 | 0.008 |
| thyroid | 0.09 | 0.078 | 0.065 | 0.018 | 0.030 | 0.004 |
| liver | 11.44 | 1.642 | 2.397 | 0.432 | 0.201 | 0.002 |
| stomach | 1.19 | 1.324 | 0.723 | 0.353 | 5.162 | 6.451 |
| small intest | 9.49 | 8.044 | 26.264 | 14.279 | 3.498 | 1.294 |
| large intest | 0.39 | 0.341 | 0.478 | 0.251 | 0.124 | 0.016 |
| feces | 0.42 | 0.500 | 0.681 | 0.402 | 1.045 | 0.469 |
| urine | 0.20 | 0.329 | 5.130 | 4.219 | 0.031 | 0.017 |

Technetium-99m labeled kit formulation according example 4:

| | 2 min | | 60 min | | 24 h | |
|---|---|---|---|---|---|---|
| organ | % ID/organ | stdev | % ID/organ | stdev | % ID/organ | stdev |
| blood | 0.24 | 0.092 | 0.022 | 0.007 | 0.002 | 0.000 |
| brain | 0.05 | 0.005 | 0.020 | 0.003 | 0.004 | 0.000 |
| pancreas | 0.60 | 0.113 | 0.352 | 0.084 | 0.018 | 0.010 |
| spleen | 0.35 | 0.093 | 0.257 | 0.032 | 0.014 | 0.003 |
| kidney | 6.22 | 0.896 | 1.701 | 0.091 | 0.098 | 0.010 |

-continued

| organ | 2 min | | 60 min | | 24 h | |
|---|---|---|---|---|---|---|
| | % ID/organ | stdev | % ID/organ | stdev | % ID/organ | stdev |
| fat | 0.07 | 0.038 | 0.041 | 0.011 | 0.006 | 0.005 |
| muscle | 0.24 | 0.006 | 0.230 | 0.105 | 0.191 | 0.105 |
| heart | 1.46 | 0.196 | 1.302 | 0.104 | 0.177 | 0.069 |
| lung | 0.51 | 0.075 | 0.285 | 0.582 | 0.026 | 0.013 |
| thyroid | 0.10 | 0.002 | 0.063 | 0.024 | 0.032 | 0.011 |
| liver | 17.81 | 1.416 | 6.117 | 1.727 | 0.435 | 0.055 |
| stomach | 1.16 | 0.259 | 0.983 | 0.316 | 0.104 | 0.025 |
| small intest | 13.75 | 1.929 | 28.599 | 0.310 | 2.750 | 0.516 |
| large intest | 0.64 | 0.082 | 0.512 | 0.055 | 0.179 | 0.034 |
| feces | 0.40 | 0.141 | 0.654 | 0.131 | 1.356 | 1.066 |
| urine | 0.61 | 0.798 | 11.314 | 1.863 | | |

Technetium-99m labeled kit formulation according example 5:

| organ | 2 min | | 60 min | | 24 h | |
|---|---|---|---|---|---|---|
| | % ID/organ | stdev | % ID/organ | stdev | % ID/organ | stdev |
| blood | 0.14 | 0.060 | 0.028 | 0.018 | 0.002 | 0.000 |
| brain | 0.05 | 0.007 | 0.028 | 0.007 | 0.005 | 0.002 |
| pancreas | 0.47 | 0.105 | 0.413 | 0.016 | 0.025 | 0.010 |
| spleen | 0.40 | 0.057 | 0.301 | 0.083 | 0.022 | 0.004 |
| kidney | 3.05 | 1.827 | 5.816 | 0.978 | 0.098 | 0.003 |
| fat | 0.05 | 0.029 | 0.041 | 0.024 | 0.003 | 0.001 |
| muscle | 0.37 | 0.167 | 0.404 | 0.261 | 0.245 | 0.013 |
| heart | 1.74 | 0.146 | 1.634 | 0.315 | 0.279 | 0.047 |
| lung | 0.97 | 0.547 | 0.372 | 0.750 | 0.024 | 0.010 |
| thyroid | 0.10 | 0.014 | 0.089 | 0.019 | 0.025 | 0.011 |
| liver | 18.31 | 5.309 | 6.320 | 2.521 | 0.532 | 0.035 |
| stomach | 1.07 | 0.028 | 1.573 | 0.469 | 0.104 | 0.021 |
| small intest | 14.61 | 1.106 | 28.227 | 5.763 | 2.337 | 0.305 |
| large intest | 0.65 | 0.047 | 0.664 | 0.155 | 0.183 | 0.010 |
| feces | 0.53 | 0.254 | 0.414 | 0.120 | 0.801 | 0.631 |
| urine | 0.06 | 0.012 | 5.752 | 5.423 | | |

The invention claimed is:

1. A stabilized form of Tetrofosmin represented by the general formula (I):

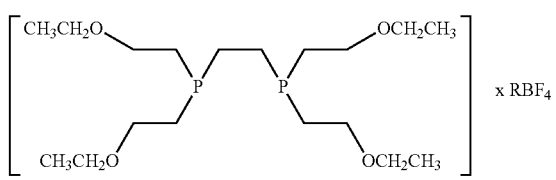

(I)

wherein R is H and x is a number between 1 and 2.

2. A stabilized form of Tetrofosmin according to claim 1 with the formula (II)

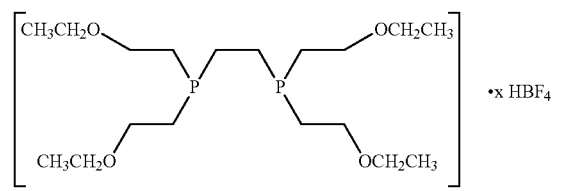

(II)

wherein x is 1 or 2.

3. A non-radioactive kit comprising at least one container, wherein one container contains a stabilized form of Tetrofosmin according to claim 1.

4. Non-radioactive kit according to claim 3, wherein the kit additionally comprises one or more of the following:
(i) reductant,
(ii) transfer ligand,
(iii) preservative,
(iv) agent for pH adjustment and
(v) fillers.

5. Non-radioactive kit according to claim 3, wherein the container is a sealed and sterilized vial, syringe bottle or ampoule.

6. Non-radioactive kit according to claim 3, wherein the storage period of the non-radioactive kit at room temperature is at least 52 weeks.

7. Non-radioactive kit according to claim 4, wherein the reductant is a tin(II) salt.

8. Non-radioactive kit according to claim 4, wherein the transfer ligand is gluconate and/or sulphosalicylate.

9. Non-radioactive kit according to claim 4, wherein the agent for pH adjustment is a hydrogen carbonate and/or a phosphate salt.

10. A non-radioactive kit comprising at least one container, wherein one container contains a stabilized form of Tetrofosmin according to claim 2.

11. Non-radioactive kit according to claim 10, wherein the kit additionally comprises one or more of the following:
(i) reductant,
(ii) transfer ligand,
(iii) preservative,
(iv) agent for pH adjustment and
(v) fillers.

12. Non-radioactive kit according to claim 10, wherein the container is a sealed and sterilized vial, syringe bottle or ampoule.

13. Non-radioactive kit according to claim 10, wherein the storage period of the non-radioactive kit at room temperature is at least 52 weeks.

14. Non-radioactive kit according to claim 11, wherein the reductant is a tin(II) salt.

15. Non-radioactive kit according to claim 11, wherein the transfer ligand is gluconate and/or sulphosalicylate.

16. Non-radioactive kit according to claim 11, wherein the agent for pH adjustment is a hydrogen carbonate and/or a phosphate salt.

* * * * *